United States Patent [19]

Axén et al.

[11] Patent Number: 4,647,655

[45] Date of Patent: Mar. 3, 1987

[54] METHOD FOR SPLITTING DI-SULPHIDE BONDS AND A COMPOUND OBTAINED THEREBY

[75] Inventors: Rolf E. Axén, Upplands Bälinge; Jan P. Carlsson; Hakan N. Drevin, both of Upsala, all of Sweden

[73] Assignee: Pharmacia Aktiebolag, Uppsala, Sweden

[21] Appl. No.: 700,819

[22] PCT Filed: May 16, 1984

[86] PCT No.: PCT/SE84/00186

§ 371 Date: Jan. 16, 1985

§ 102(e) Date: Jan. 16, 1985

[87] PCT Pub. No.: WO84/04525

PCT Pub. Date: Nov. 22, 1984

[30] Foreign Application Priority Data

May 17, 1983 [SE] Sweden ............................... 8302758

[51] Int. Cl.$^4$ ..................... A61K 39/395; C07K 15/00; C12N 9/96
[52] U.S. Cl. ....................................... 530/390; 424/85; 435/188; 530/345; 530/404; 530/408; 530/388; 546/193; 546/261; 546/270; 546/281; 546/291; 546/294
[58] Field of Search ..................... 260/112.5 R, 112 R, 260/112 B; 435/188; 530/390, 345, 388, 404, 408; 546/193, 261, 270, 281, 291, 294; 424/85

[56] References Cited

U.S. PATENT DOCUMENTS

| 4,149,003 | 4/1979 | Carlsson et al. ............ 260/112 R X |
| 4,175,073 | 11/1979 | Carlsson et al. ............ 260/112 R |
| 4,232,119 | 11/1980 | Carlsson et al. ............ 260/112 R X |
| 4,237,267 | 12/1980 | Okuyama et al. ............ 435/188 |
| 4,258,193 | 3/1981 | Fujii et al. ............ 260/112.5 R X |
| 4,511,501 | 4/1985 | Luduena ............ 260/112 R |

FOREIGN PATENT DOCUMENTS

| 0063109 | 10/1982 | European Pat. Off. . |
| 0064040 | 11/1982 | European Pat. Off. . |
| 82/03394 | 10/1982 | PCT Int'l Appl. ............... 435/188 |

Primary Examiner—Howard E. Schain
Attorney, Agent, or Firm—Fred Philpitt

[57] ABSTRACT

There is described a method for splitting at least one disulphide bond —S—S—, where each of the sulphur atoms is directly bound covalently to its respective aliphatic carbon atom in an organic substance which contains at least one such disulphide bond, in which each bond —S—S— which is split is converted substantially to two reactive groups of the formulae —S—S—$R_1$ and $R_2$—S—S—, where $R_1$ and $R_2$ are equal or different and each is an organic residue. Splitting of the bond is effected by reacting said organic substance with a mixture of a compound $R_3$—S—S—$R_4$ and a compound capable of existing in the tautomeric forms $R_5$—S—H and $HR_5$=S or corresponding resonance-stabilized anion forms, in which compounds the residues $R_3$, $R_4$ and $R_5$ (i) are organic residues of which all are different, two are equal or all are equal, and (ii) are defined in (a) that each of the aforesaid sulphur atoms in the compounds $R_3$—S—S—$R_4$ and $R_5$—S—H is bound to a carbon atom in an aromatic ring and (b) that under prevailing splitting conditions a compound $R_3$—S—H or $R_4$—S—H released by the reaction of the compound $R_3$—S—S—$R_4$ and the compound $R_5$—S—H exist substantially in their tautomeric forms $HR_3'$=S, $HR_4'$=S and $HR_5'$=S respectively, or corresponding resonance-stabilized anion forms. In each of the groups —S—S—$R_1$ and $R_2$—S—S— produced by splitting the disulphide bond, $R_1$ and $R_2$ are each a residue of the group which consists of $R_3$, $R_4$ and $R_5$. The invention also relates to an organic compound produced by the aforesaid splitting and exhibiting at least one group —S—S—$R_1$ and/or $R_2$—S—S— bound covalently to an aliphatic carbon atom, in which groups $R_1$ and $R_2$ have the aforegiven significance.

5 Claims, No Drawings

METHOD FOR SPLITTING DI-SULPHIDE BONDS AND A COMPOUND OBTAINED THEREBY

The present invention relates to a method for splitting at least one disulphide bond, —S—S—, in which each of the sulphur atoms is bonded covalently directly to a respective aliphatic carbon atom in an organic substance containing at least one such disulphide bond, each bond —S—S—, which is split, being substantially converted to two reactive groups of the formulae —S—S—$R_1$ and $R_2$—S—S—, where $R_1$ and $R_2$ are the same or different and each is an organic residue. The invention also relates to an organic compound which exhibits at least one group —S—S—$R_1$ and/or $R_2$—S—S— bound covalently to an aliphatic carbon atom, in which groups $R_1$ and $R_2$ have the aforesaid significance.

Aliphatic thiol groups (i.e. the thiol group is bound to an aliphatic carbon atom) and disulphide groups derived therefrom have an important part to play in biochemical contexts. Thiol groups react under physiological conditions with a multiplicity of other functional structures, such as active thioesters for example. Thiol groups are often found in the active sites of enzymes, in which case they play an important part in the catalytic activity of the enzyme. Disulphide groups are often present in polypeptides (which term is also considered to include proteins) and usually appear to act as fixing elements and elements which afford conformation. The part played by natural disulphides as a reagent in the context of dynamic biochemical reactions is relatively unknown, but must be considered to be of great significance, for example through the aforementioned conformational properties in connection with proteins (c.f. for example FEBS Letters 97 [1979] pages 201-10).

The type of reaction involving both thiol groups and disulphide groups at the same time is designated thiol-disulphide-exchange and can be written as:

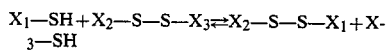

where $X_1$, $X_2$ and $X_3$ are organic residues which contain an aliphatic or an aromatic carbon atom which is bound to one of the sulphur atoms in —S—S—.

Although the thiol-disulphide-exchange reaction takes place rapidly under physiological conditions, the conditions of equilibrium are normally unfavourable for the preparative production of a given disulphide. For example, when a polydisulphide is mixed with a thiol component, there rapidly takes place a series of thiol-disulphide-exchange reactions which result in a complex mixture of various disulphide-containing entities. If the polydisulphide is a biologically active molecule, the activity is affected.

The intriductions of so-called reactive disulphides, e.g. of the alkyl pyridyl disulphide type, has greatly facilitated the preparation of disulphides. By reactive disulphide is normally meant a disulphide of increased electrophilicity and of such nature that departing thiols are transformed to a stabilized tautomeric thioneform or the stabilized anion thereof. This stabilization denies the departed thiols the possibility of taking part in reverse or retro-reactions, e.g. in the case of alkyl pyridyl disulphide, aliphatic thiol-structures are not split off, but thione structures are. In this way, there is obtained an equilibrium which is favourable to the preparation of desired aliphatic disulphide.

Processes which are based on thiol-disulphide-exchange reactions and involve biologically active molecule types are now used increasingly in the conjugation of biomolecules with carrier polymers or biomolecules with biomolecules, whereby in the former case the external properties of the biomolecules, such as their solubility, separability, stability, transportability, are changed to fulfil given requirements, while in the latter case a multiple of bio-activities are combined and caused to coact, e.g. immunological properties with enzymatical properties or pharmacological properties with homing properties. Such preparations have found use, or can be judged to find future use in connection with chromatography, pharmaceuticals, diagnostic analysis methods, and in process technology.

Methodology in the preparation of disulphide conjugates by means of reactive disulphides between components which do not contain thiol groups has often involved the reaction of the components with particular thiolating reagents, for example homocystein thiolactone and thiolimidates, or with bifunctional reagents, for example the bifunctional reagent N-succinimidyl-3-(2-pyridyldithio)-propionate. Thus this last-mentioned compound permits reactive disulphide to be introduced directly into, for example, protein molecules, but, because of the ease of reduction, also the introduction of thiol-groups.

If a component contains an aliphatic disulphide bond (i.e. a disulphide bond between two aliphatic carbon atoms) and it is intended to be conjugated as a disulphide with another component, which is quite usual in respect of proteins, it has been possible, in principle, first to reduce the aliphatic disulphide bond and then to react the resultant thiol groups with reactive disulphide of the other component, (c.f. for example Immunology Letters, 2 (1980) 151–155 or Haemotologia 14 (1981) 95–99).

This known method is encumbered with a number of disadvantages, however. The reduction process is normally effected with aliphatic thiol-compounds of low molecular weight. In order to achieve a partial reduction of a polydisulphide, a moderate concentration of low-molecular thiol compound is used, thiol-disulphide-exchange reactions, however, being also initiated within the polydisulphide molecule as mentioned above. Total reduction of polydisulphide can be achieved with a high concentration of low-molecular aliphatic thiol (more often than not, together with a denaturing agent). When such reaction mixtures are worked up, however, the concentration conditions readily change, so that partial retro-reactions take place. In addition, difficulties in avoiding oxidation of the reaction-prone thiol structures with air are always liable to occur. The possibility of avoiding separation at the thiol stage, and inhibiting the equilibrium mixture with, for example dipyridyldisulphide is not really practicable, since dipyridyldisulphide is consumed by the reducing agent, and the asymmetric reactive disulphides initially formed initiate reformation of a reduced polydisulphide component, both intermolecularly, and also together with the reducing agent.

Sulphitolysis with sodium sulphite is an old, known method of cleaving disulphides which has been applied in the field of protein chemistry for the total splitting of multi-chain peptides into polypeptide fractions (c.f. the references cited above). The methodology is difficult to control, however, and requires the use of catalytic quantities of, for example, cystein and oxygen. The advantage afforded is that the method provides the thiol function with a protective group of S-sulphonate structure.

A greater part of the disadvantages encountered with these earlier known methods is eliminated by means of the present invention. Splitting of a disulphide bond in accordance with the invention is characterized in that splitting is effected by reacting the organic substance containing at least one, preferably aliphatic disulphide bond which is to be split, with a mixture of a compound $R_3$—S—S—$R_4$ and a compound which can exist in the tautomeric forms $R_5$—S—H and $HR_5'$=S or the corresponding resoncance-stabilized anion form, in which compounds the residues $R_3$, $R_4$, $R_5$
(i) are organic residues, of which all are different, two are the same or all are the same, and
(ii) are defined in
  (a) that in the compounds $R_3$—S—S—$R_4$ and $R_5$—S—H, each of said sulphur atoms is bound to a respective carbon atom in an aromatic ring, and
  (b) that a compound $R_3$—S—H or $R_4$—S—H released through the reaction of the compound $R_3$—S—S—$R_4$, and the compound $R_5$—S—H under prevailing splitting conditions substantially exist in their respective tautomeric forms $HR_3'$=S, $HR_4'$=S and $HR_5'$=S or corresponding resonance-stabilized anion forms; and that $R_1$ and $R_2$ are each a residue of the group which consists of $R_3$, $R_4$ and $R_5$.

The splitting according to the invention can be considered an oxidation since in one stage said splitting oxidizes a disulphide-containing compound by converting at least one of its disulphide bonds to two new disulphide bonds. Previously, splitting methods have been reductive, in that the splitting process has involved the reduction of one disulphide bond to two thiol groups.

In the aforegoing $R_3$—S—H, $R_4$—S—H and $R_5$—S—H represent the compounds in their thiol-forms, and $HR_3'$=S, $HR_4'$=S and $HR_5'$=S represent said compounds in their thione-form. A thiol-form and corresponding thione-form is an example of thiol-thione-tautomerism which is fully analogous with enol-keto-tautomerism. Both types of tautomerism are well known and imply that a thiol group (hydroxyl group) which is bound to an $sp^2$-hydridized carbon atom can be transformed intramolecularly to a thione group (keto group). The transformation implies that a hydrogen has changed place in the molecule, while the double bonds have changed position at the same time, i.e. $R_3$, $R_4$ and $R_5$ only differ from $R_3'$, $R_4'$ and $R_5'$ respectively in respect of the location of the double bonds. The expression is well known to all organic chemists. Both thione and ketone forms can be transformed to their respective resonance-stabilized, deprotonized anion forms by basic substances. In the case of the above-mentioned thione forms, these anions are designated $\ominus R_3'$=S, $\ominus R_4'$=S and $\ominus R_5'$=S.

Hereinafter, the unstable thiols $R_3$—S—H, $R_4$—S—H and $R_5$—S—H will be referred to as thiones, since under the prevailing splitting conditions they exist in their stabilized thione form or corresponding anion form.

Splitting effected in accordance with the invention enables, in a single step, an aliphatic disulphide bond to be converted to two reactive disulphide structures which are inert during the splitting process, such as to enable isolation of at least one compound containing one of the resultant reactive disulphide structures —S—S—$R_1$ and —S—S—$R_2$.

The splitting of an aliphatic disulphide bond in accordance with the invention in an organic substance containing one such bond can be illustrated schematically in the following manner:

$$A_1-S-S-A_2 \quad A_1-S-S-R_1 \quad R_2-S-S-A_2,$$

in which $A_1$ and $A_2$ each signify remaining parts of the organic substance, and in which the broken line signifies that $A_1$ and $A_2$ may possibly be jointed together with a bond other than the —S—S— bond to be split. Thus, when $A_1$ and $A_2$ are not linked by a bond other than the —S—S— bond to be split, two new molecules are obtained. Thus when $A_1$ and $A_2$ are linked to each other also with a bond other than the —S—S— bond to be split, one new molecule is obtained. The invention also embraces an organic compound which exhibits at least one group —S—S—$R_1$ and/or $R_2$—S—S— bound covalently to an aliphatic carbon atom, which organic compound arises from such splitting.

Splitting of the aforesaid bond in accordance with the invention can be effected without needing to apply extreme pH-conditions. This enables hydrolytic side reactions to be avoided. For example, it is possible in this way to avoid hydrolysis of the disulphide bond to be split, or hydrolysis of other hydrolysis-sensitive bonds, such as amide, peptide, ketal, acetal or ester bonds for example. Consequently, the invention affords a bond-splitting method which transforms an aliphatic disulphide bond into two reactive disulphide structures, in a selective and specific fashion.

The splitting reaction is pH-dependent, and can be effected in aqueous media at pH 5-12. In order to avoid the occurrence of side reactions when dealing with sensitive substances, the pH-value should be within the range of 7 to 11.

The most important advantages afforded by the invention are based on the surprising discovery that the different types of disulphide bonds of a polypeptide can be split stepwise, i.e. as the excess reactive disulphide $R_3$—S—S—$R_4$ and the amount of $HR_5$=S increases, each bond-type is split only at its own particular excess. Naturally, this will only apply when remaining conditions are kept constant. The aforesaid discovery affords important advantages preparatively, since it enables unitary products to be obtained, i.e. products in which disulphide bonds equivalent in type and number are split in every molecule.

Thus, splitting in accordance with the invention also provides a method for splitting at least one disulphide bond to all the disulphide bonds of a polydisulphide. Particularly important advantages are obtained when the split disulphide bond is contained in a biologically active macromolecule, such as a protein or a polypeptide for example, which contain, almost without exception, at least one cystine structure. In the case of compounds such as these, the biological activity may be retained to a greater extent than that afforded by earlier known disulphide-bond splitting methods. The fact that it is possible to achieve such an unusually high biological activity is probably because no intermolecular and intramolecular thiol-disulphide-exchange reactions take place during the process of the method according to the invention. Presumably, this is because there are no aliphatic thiol groups present during the splitting process. If such groups are present at all, then it is only to a very small extent. Particularly important advantages are afforded when the polydisulphide does not contain any free thiol groups capable of reacting with added reactive disulphide $R_3$—S—S—$R_4$. Low molecular-weight thiol compounds readily initiate intramolecular thiol-disulphide-exchange reactions. Consequently, such compounds should not be present during the splitting process.

A large number of thiol compounds tautomerize to their thione form spontaneously in aqueous solutions, i.e. the thione forms of such compounds is more stable than their corresponding thiol form. One requisite in this regard is that the sulphur atom of the thiol group should be bound to an $sp^2$-hybridized carbon atom in an aromatic ring. The thione form is still further stabilized, when the aromatic ring includes a heteroatom (i.e. when the ring is heterocyclic), preferably nitrogen, and/or is provided with at least one electron-attracting substituent selected, for example, from the group: nitro, cyano and carboxy. The sulphur atom is preferably located at a distance from a heteroatom in a heterocyclic aromatic ring equal to an odd number of atoms. With respect to the splitting reaction, it is extremely important that the structure of the thiols $R_3SH$, $R_4SH$ and $R_5SH$ is such as to permit transformation and stabilization to respective thione form or corresponding resonance-stabilized anion form to take place. In this respect, stabilization shall be of such a high level that the thione and anion forms are thermodynamically denied from thiol-disulphide-exchange reactions under the prevailing splitting conditions. Consequently, electron-attracting substituents are always required in the aforesaid non-heterocyclic ring systems, in order to achieve stabilization of the thiol form to corresponding thione or anion form.

Examples of $R_3$, $R_4$ and $R_5$ whose thiol compounds are stabilized spontaneously under prevailing splitting conditions to corresponding thione forms by tautomerism or resonance include: 5-nitro-2-pyridyl, 5-carboxy-2-pyridyl, 2-pyridyl, 4-pyridyl, 2-benzothiazolyl, 4-nitro-3-carboxy-phenyl and the N-oxides of the above pyridyl groups. In the reactive disulphide compounds $R_3$—S—S—$R_4$, which are preferably symmetrical, both $R_3$ and $R_4$ are suitably selected from 5-nitro-2-pyridyl, 5-carboxy-2-pyridyl, 2-pyridyl, 4-pyridyl, 2-benzothiazolyl, 4-nitro-3-carboxyphenyl and the N-oxides of the above pyridyl groups. Both reactive disulphides $R_4$—S—S—$R_3$ and thions $HR_5'$=S, which correspond to these groups, are readily available, and consequently are those preferred most, for use in the splitting method of the present invention.

As will be understood, when a hydrogen atom in any of these groups is replaced with a substituent having an aliphatic carbon atom bound next to the aromatic ring, the corresponding thiol will then be spontaneously stabilized to its thione form.

The invention also provides a method for splitting an aliphatic disulphide bond in a low molecular compound which exhibits such a bond. Examples of such compounds include cystine and carboxyl and amino derivatives thereof. Another example is the splitting of the —S—S—bond in thioctic acid and its carboxyl derivative. Substances which affect the conformation of a polydisulphide can be added to the reaction mixtures, thereby to influence the extent to which splitting takes place. For example, when the polydisulphide is a protein, a higher degree of splitting can be achieved by adding urea and/or a detergent. These two substances influence the splitting process, by breaking hydrogen bonds, so as to alter the conformation.

The disulphide bonds, which are split, are aliphatic. By this is meant, both in the description and in the claims, that each of the sulphur atoms of the bond is bound to its respective aliphatic carbon atom to which no other atom is bound other than carbon and/or hydrogen. Thus, those carbon atoms to which the sulphur atoms can be bound are primary, secondary, tertiary carbon atoms, and also the carbon atom in a methyl group.

When selecting reactive disulphide $R_3$—S—S—$R_4$ and thione, a particular advantage is afforded when the disulphide and thione chosen are such that $R_3=R_4=R_5$. Such a choice will result in highly uniform product mixtures ($R_1=R_2=R_3=R_4=R_5$) and utilizes readily available reagents.

The magnitude of the practicable excess of thione and reactive disulphide $R_3$—S—S—$R_4$ is primarily determined by their solubility. Disulphides and thiones which contain electrically charged groups, e.g. negatively charged carboxylate groups, are more soluble in aqueous media than those which are not electrically charged. Consequently, when a large number of disulphide bonds are to be split it is more advantageous to select reactive disulphides $R_3$—S—S—$R_4$ and thiones which are highly soluble.

When splitting of disulphide bonds is effected in non-polar solvents, non-polar disulphides $R_3$—S—S—$R_4$ and thiones are preferably selected, since these have the greatest solubility in such solvents.

The extent to which splitting is achieved is controlled by the molar concentration of thione and reactive disulphide $R_3$—S—S—$R_4$ in the reaction mixture, and by their respective concentration in relation to the concentration of aliphatic disulphide bonds. The extent to which splitting is effected can be increased by means of a large excess of thione and reactive disulphide $R_3$—S—S—$R_4$.

Consequently, in accordance with the invention, the molar initial concentrations of thione $HR_5'$=S and reactive disulphide $R_3$—S—S—$R_4$ relative to the initial concentration of aliphatic disulphide bonding, is so chosen as to obtain the degree of splitting intended.

In order to run the reaction, the initial concentration of reactive disulphide, $R_3$—S—S—$R_4$, should be so selected as to be in a molar excess, e.g. up to 1000 times greater than the corresponding concentration of the aliphatic disulphide bonds. Normally, the absolute value of the concentration of said reactive disulphide is selected in the range of 0.1–400 mM. The thione concentration is normally selected so as to be from 5 to 100 times greater than the initial concentration of aliphatic disulphide bonds. In this regard, the thione absolute-value should lie within the range of 0.1–400 mM, although in order to achieve the desired degree of splitting within a reasonable length of time, it is often suitable to select a thione absolute-value from the range 10–400 mM. The upper limits of the above ranges are all determined by the solubility of the reactive disulphide and the thione in the reaction medium. If they are highly soluble, their respective concentrations can be extended beyond the limits stated, resulting in a higher possibility of a greater degree of splitting and higher splitting rates.

It will be understood, that the precise molar proportions and quantities are contingent on the choice of $R_3$, $R_4$ and $R_5$, and on the aliphatic structure of the aliphatic disulphide bond. One of average skill in this field, however, is well able to establish how the reaction should be controlled, with the aid of the general guide lines given above.

Splitting of the disulphide bonds is advantageously effected in an aqueous solvent. Various solvents can be added, in order to improve the solubility of the various reagents (reactive disulphide $R_3$—S—S—$R_4$ and thion). Naturally, the solvent added must not have a deleterious effect on the splitting process. For example, it must not impair the aforesaid stabilization of the thiols $R_3$—S—H, $R_4$—S—H and $R_5$—S—H to respective thiones. Neither must it be allowed to impair the biological activity, when it is desired to retain such activity.

Conveniently, the splitting process is effected at a temperature which does not favour side reactions. With respect to biologically active substances, for example, polypeptides which contain cystine, it is essential that the temperature selected will not cause denaturation of the polypeptide, if the activity is to be maintained. The number of disulphide bonds split by the process is also contingent upon the temperature.

Substances containing aliphatic disulphide bonds, in which a disulphide bond is to be split, are usually soluble in the liquid phase in which splitting takes place, although insoluble substances containing aliphatic disulphide bonds can also be split in accordance with the invention. For example, it is possible to split aliphatic disulphide bonds which are bound covalently to an insoluble polymer, e.g. an insoluble porous polymer containing hydroxyl and/or amino groups. Examples of such insoluble polydisulphides include agarose, dextran cross-linked with epichlorohydrin, poly(hydroxymethacrylates) etc. to which covalently bound aliphatic disulphide groups are substituted. Products obtained by means of the invention can be used within different fields, examples of which are given below.

The introduced disulphide structures $R_1$—S—S— and $R_2$—S—S— are both reactive to aliphatic thiol groups and can therefore be used to couple a splitting-product with a thiol-containing compound, via a thiol-disulphide-exchange reaction. The product thus obtained is a so-called conjugate. The term conjugate generally implies two compounds bound together covalently.

An important type of conjugate which can be produced from the products obtained when splitting disulphide bonds in accordance with the invention (hereinafter called splitting-products) is that which is obtained when a compound which can be indicated analytically is conjugated with a ligand or receptor in which at least one disulphide bond has been split. By receptor or ligand is meant here pairs of compounds which have a biospecific affinity for one another. Examples of such pairs include: antibody-antigen (hapten), Protein A-IgG (immunocomplex), lectin-carbohydrate, Thyroxin-TBG, enzyme-substrate, enzyme-coenzyme etc. As will be understood, fragments of a ligand or a receptor which have retained their biospecific affinity shall also be considered to be a ligand or receptor.

The reference to a compound which can be indicated analytically is directed to a compound which can be detected either in the conjugate or freed therefrom. Examples of such compounds are those which are enzymatically active (i.e. enzymes, enzyme substrates, cofactors, cosubstrates, co-enzymes, etc.) and fluorescent, phosphorescent, chemiluminescent, radioactive, metal-containing compounds etc. (c.f. for example Schall RF et al; Clin Chim 27 (1981) pages 1157–81).

The conjugates containing analytically indicatable groups can be used to detect various substances quantitatively and qualitatively. A conjugate between an antibody and an analytically indicatable compound can be used, for example, to assay corresponding native antibodies or the antigen or hapten against which the antibody is directed. In this respect, the assay can be effected in a liquid sample taken from a mammal, for example in a sample in which the substance to be assayed is present in a dissolved form. Particular mention can be made in this respect to various heterogenous and homogenous methods set forth in the claims of U.S. Pat. No. 3,817,837 and U.S. Pat. No. 4,231,999, and described as the state of the art therein. The aforesaid conjugates can also be used to assay cell-bound or organelle-bound ligands and receptors to which the conjugate exhibits a biospecific affinity. This can take place, inter alia, with the aid of different microscopy methods.

Another type of conjugate is that obtained when the splitting product is permitted to react with thiol groups on an insoluble carrier. When the splitting-product is derived from a disulphide-containing receptor or ligand, there can be obtained conjugates which are particularly well suited as the solid phase for affinity chromatography and for the afore-mentioned heterogenous assaying methods.

A third type of conjugate is that obtained when a receptor is split in accordance with the invention and conjugated with a thiol-containing therapeutically active compound, for example conjugates analogous with those described in No. EP-A-0 023 401, No. EP-A-0 017 507, No. EP-A-0 023 779. If the receptor is an antibody which is directed against a specific type of cell (so-called target cell) such as a cancer cell, the conjugate when administered to mammals will selectively bind to its target cell. The therapeutically active compound should therefore be more efficient.

Among other potential types of conjugates which can be produced can be mentioned disulphide conjugates for immunizing purposes. Such conjugates can be produced from a protein antigen which contains splittable disulphide bonds. Subsequent to splitting the bonds in accordance with the invention, the conjugate is formed when the splitting product is reacted with a thiol-containing soluble or insoluble carrier.

In accordance with the invention, the splitting products obtained can also be used directly, without preforming conjugates. For example, it is known from No. EP-A-0 064 04 and No. EP-A-0 063 109 that therapeutically active compounds containing asymmetric reactive disulphide structures of the type $R_1$—S—S—, may exhibit a prolonged therapeutical effect, compared with corresponding therapeutically active compounds which do not have this structure. Therapeutically active disulphide compounds which can be split in accordance with the invention without irreversably destroying the activity of the compounds can thus be transformed, in a novel manner according to the invention, to compounds in which the therapeutical activity may prevail for a prolonged period of time.

In the aforegoing, mention has been made of therapeutically active compounds which can be obtained by means of the present invention. Whenever these products are administered, there is delivered a therapeutically active dosage. The preparations employed may have the form of an emulsion, a solution, tablet, etc. which may optionally contain a pharmaceutically acceptable carrier and also optionally a suitable adjuvant. The conjugates are preferably administered through subcutaneous or intravenous injections. Therapeutically active splitting products can be administered by the same route, but administration by other routes is also possible for said splitting products, as well as for the conjugates.

As will be understood, in the case of the splitting-products, each property incorporated per se in the structures $R_1$—S—S— and $R_2$—S—S— can be utilized directly.

The greatest advantages afforded by the method according to the invention over previously known methods for introducing asymmetric reactive disulphide structures are obtained in respect of biologically active polydisulphides, e.g. cystine-containing polypeptides, such as immunoglobulins, particularly antibodies. By means of the splitting method according to the invention it is possible to split one and the same disulphide bond in each molecule. If only a part of the total number of bonds present are split, e.g. if one, two or three bonds are split in an immunoglobulin, such as an antibody, it is possible to retain the tertiary structure of the polypeptide to a greater extent than that afforded by previously known methods. This means that in cases such as these, the splitting-products are particularly homogenous with respect to the positioning in the molecule of the introduced structures. This also results in the formation of particularly homogenous conjugates, so as to enable the production, for example, of good immunoadsorbents, in which the antigen-binding parts of all antibodies are pointing in the same direction. This also applies to the other conjugates. The homogeneity can be further increased when antibodies which derive from the same cell-line are split and conjugated, i.e. when so-called monoclonal antibodies are used.

The aforegoing description of the various usages to which the invention can be put has only been given by way of example and is not meant to limit the scope of the invention in any way. This is also true of the Examples given hereinafter.

EXAMPLE 1

Splitting of disulphide bond in IgG

Immunoglobulin of type IgG was produced from sheep, by gel-filtration of immunosorbent pure sheep-antirabbit-IgG anti-serum on allyl dextran cross-linked with N,N'-methylene-bis-acrylamide (Sephacryl® S-300 from Pharmacia Fine Chemicals AB, Uppsala, Sweden). The IgG-antibodies (28 μM) were incubated with 5 mM 2,2'-dipyridyl disulphide and different concentrations of 2-thiopyridone (see Table 1, first column) in 40 mM sodium phosphate buffer with 0.21 M sodium chloride and 10% ethanol at 23° C. for 24 hours in a volume of 5 ml. Subsequent to the reaction, the reaction mixtures were separated on columns containing dextran cross-linked with epichlorohydrin (Sephadex® G-25M from Pharmacia Fine Chemicals, Uppsala, Sweden) in 0.1M sodium phosphate buffer, pH 8.5, the protein fractions being collected. The content of groups which could be split to 2-thiopyridone was determined in accordance with Biochem. J. (1968) 173, 723–737, (c.f. Table 1, second column). The following results were obtained:

TABLE 1

| (2-thiopyridone) (mM) | Equivalents of 2-thiopyridyl structures per IgG-equivalent. |
|---|---|
| 12.5 | 0.89 |
| 25 | 1.23 |
| 50 | 1.52 |
| 100 | 1.86 |
| 200 | 2.00 |

EXAMPLE 2

Splitting of disulphide bonds in fragments of rabbit anti-human IgE-antibody of the IgG class Rabbit anti-human IgE-antibodies of the IgG-class were prepared by immunising rabbits with Fc-fragments of human IgE(N.D.). The anti-serum was purified by immunosorption on immobilized peptide fragments of IgE, in order to provide anti-IgE antibodies directed against the $DE_2$-domains of the Fc-portion of the IgE-molecule (Advances in Immunology Vol 13 (1971) (AP)). 2.07 mg of purified antibodies in 1.0 ml of sodium acetate buffer, pH 4.5, were cleaved with 50 μg pepsin (designation 3,4,23 from Worthington Biochemical Corporation, Freehold, N.J., USA) at 37° C. over a period of 24 hrs (Handbook of Experimental Immunology, Wein 6-20 to 6-22).

The pepsin was then destroyed by adjusting the pH of the solution to 8.0 with a 0.1M sodium phosphate buffer, pH 11.2 (about 750 μl). 24 mg of 2-thiopyridone (Ega-Chemie, Steinheim, Federal Republic of Germany) and 2.4 mg of 2,2'-pyridyldisulphide (Fluka AG, Buchs, Switzerland) were added to the solution, which was then rotated "end over end" at a temperature of 23° C. for 18 hours. Subsequent to centrifugation, the reaction mixture was separated on a column packed with approximately 200 ml Sephacryl® S-300 in 0.3M saline. The main protein peak having a molecular weight corresponding to 56,000 g/mole, which corresponds to the molecular weight of the Fab'-fragment of IgG (Handbook of Experimental Immunology, Wein 6-20 to 6-22) was collected and concentrated under an $N_2$-gas environment in a 25 ml concentrating cell (model 12 from Amicon Corp, Lexington, Mass, USA) on a PM-10-filter. 0.5 ml concentrate was obtained with $A_{280}$=1.09 (1 cm cell). The content of groups which could be split to 2-thiopyridone was determined subsequent to reduction with dithiothreitol (Sigma Chemical Company, St. Louis, Mo., USA), to $17 \cdot 10^{-6}$M, through absorbance assaying at 343 nm. Calculations showed that the degree of substitution (equivalents of groups which could be split to form 2-thiopyridone for each equivalent Fragment) was 1.3 (Biochem. J. (1978) 173, 723–737). The absorbence of the Fragment at 280 nm was taken to be the same as that of IgG $A_{280}{}^{1\%}$=13.8 (1 cm cell).

EXAMPLE 3

Splitting of insoluble aliphatic disulphide

Agarose gel (Sepharose® 6B from Pharmacia Fine Chemicals, Uppsala, Sweden) was treated with 1-chloro-2,3-epoxypropane (0.45 ml reagent/3 g gel) with sodium thio-sulphate and reduced with dithiothreitol, as described by Brocklehurst et al. (Biochem J. 133 (1973) 573–584). The resultant thiolagarose gel (about 750μ-equivalents of thiolgroups/g of agarose) was then oxidized with hydrogen peroxide in water, to form a disulphide-agarose gel. The agarose concentration was 2% (w/v), the hydrogen peroxide concentration 0.1M and the reaction time 60 minutes. Subsequent to this oxidation, the agarose gel was washed in water and 0.05M sodium phosphate buffer, pH 9.0, with 50% ethanol added thereto. The disulphide gel was then allowed to react with 2-thiopyridone (1.0M) and 2,2'-dipyridyl disulphide (0.5M) in 50% ethanol at pH 9.0 under agitation for 120 minutes at a temperature of 23° C. The gel was then washed with 50% ethanol and water. The product was analysed by assaying 2-thiopyridone photometrically at 343 nm, after reductive splitting (Acta Chemica Scandinavica B29 (1975) 471–74). It contained 635μ-equivalents 2-thiopyridyl structures per gram of agarose.

EXAMPLE 4

Splitting of disulphide bonds in chymotrypsinogen 20 mg of chymotrypsinogen A (Millipore Corp., Bedford, Mass., USA) were dissolved in 0.5 ml of 1.0M sodium borate buffer, pH 9.0, whereafter there were added 4.5 ml of 1.86 mM 2,2'-dipyridyl disulphide-16.3 mM 2-thiopyridone. The solution was incubated at 22°, 30° and 37° C. for 80 hours. Subsequent to being centrifuged the reaction mixtures were de-salted on columns packed with dextran cross-linked with epichlorohydrin (Sephadex ® G-25M from Pharmacia Fine Chemicals AB, Uppsala, Sweden) in 0.1M sodium phosphate buffer, pH 7.0. The result of the reaction was established by the $A_{280}$-assaying and absorbence-measuring of dithiothreitol-split 2-thiopyridone, at 343 nm (Biochem. J. (1978), 173, 723–737).

The following results were obtained:

TABLE 2

| Equivalents thiopyridyl structures/ chymotrypsinogen equivalent | Reaction temperature °C. |
| --- | --- |
| 0.15 | 22 |
| 0.42 | 30 |
| 2.0 | 37 |

EXAMPLE 5

Splitting of disulphide bonds in fragments of IgG

Rabbit-IgG (from Miles Scandinavia, Birkerod, Denmark) was fragmentated with pepsin (1:100, w/w) in 0.1M sodium acetate buffer, pH 4.5, at 37° C. for 24 hours. The F(ab')$_2$-fragments were separated from the reaction mixture on a column packed with allyl dextran crosslinked with N,N'-methylene-bis-acrylamide (Sephacryl ® S-300 from Pharmacia Fine Chemicals, Uppsala, Sweden) (Handbook of Experimental Immunology, Wein 6-20 to 6-22). The concentration of fragments was determined by $A_{280}$-measurement: $A_{280}^{1\%} = 1.38$ (1 cm cell). Solutions of 23.3 μM F(ab')$_2$-fragments in 0.1M sodium phosphate solution, pH 8.0, with 2.4% ethanol and 2.0 mM 2,2'-dipyridyl disulphide (Fluka AG, Buchs, Switzerland) and different concentrations of 2-thiopyridone, were incubated over various lengths of time at 23° C. The reaction was interrupted by de-salting on beds of dextran cross-linked with epichlorohydrin (Sephadex ® G-25F from Pharmacia Fine Chemicals AB, Uppsala, Sweden), the protein fraction being collected and analysed with respect to its protein content ($A_{280}$) and to its content of reductively cleavable 2-thiopyridone ($A_{343}$) (Biochem. J. (1978) 173, 723–737). The substitution degree (= the number of equivalents of 2-thiopyridyl disulphide structures per equivalent fragment) was calculated.

The following results were obtained:

TABLE 3

| (2-thiopyridone) (mM) | Incubation time (hr) | | | |
| --- | --- | --- | --- | --- |
|  | 5 | 24 | 48 | 96 |
| 5.4 | 2.07 | 2.83 | 2.32 | 2.60 |
| 10.7 | 2.10 | 2.76 | 2.27 | 2.45 |
| 21.5 | 1.81 | 2.66 | 2.25 | 2.49 |

EXAMPLE 6

Splitting of disulphide bonds in oxidized glutathione 2.27 mmoles of 2-thiopyridone, 2.27 mmoles of 2,2'-dipyridyl disulphide and 0.23 mmole of oxidized glutathione (from Calbiochem AG, Lucerne, Switzerland) were dissolved in 45 ml of 33% Et OH, whereafter 2.0M sodium hydroxide were added to a pH of 8.1. Subsequent to reaction for 4 hours at 40° C., there were added 200 μl of concentrated acetic acid, whereafter the solution was evaporated in a rotary evaporator, to obtain 4–5 ml of partially crystallized solution. The supernatant was centrifuged at 3000×g for 10 minutes. Remaining crystals were leached with 4 ml of distilled water, whereafter the solution was centrifuged in the manner aforedescribed. The combined, centrifugal solutions (7.3 ml) were extracted twice with 3 ml portions of benzene, whereafter the water phase was evaporated to dryness in a rotary evaporator. The crystals were dissolved in a mixture of 2 ml of ethanol, 1 ml of water, and 100 μl of concentrated acetic acid. 600 μl of the solution were placed on a thin-layer plate (Merck DC-Alufolien Kiesel-gel 40, from Merck AG, Darmstadt, Federal Republic of Germany), which was developed with 10% benzene-10% acetic acid-60% ethanol-20% water. A zone on the thin-layer plate having an Rf of 0.38 was scraped out, whereafter the powder was extracted with 4 ml of water. The solution was centrifuged at 3000×g for 10 minutes and evaporated. The crystals remaining after said evaporating process were dissolved in a mixture of 1000 μl of ethanol, 500 μl of water, and 50 μl of acetic acid. Undissolved material was decantered off, whereafter the solution was evaporated to dryness in a rotary evaporator.

The product was analysed with respect to its content of groups which could be split reductively to 2-thiopyridone (Biochem. J. (1978) 173, 723–737) and with respect to amino acids in accordance with the Moore-Steins method.

It was found that the product contained one mole of reductively splittable 2-thiopyridone for each mole of cysteine. The same applied to the remaining amino acids of the product, i.e. glutamic acid and glycine.

The product was analysed on a thin-layer plate (Merck DC-Alufolien Kieselgel-60 from Merck AG, Darmstadt, the Federal Republic of Germany) with 2-thiopyridone, 2,2'-dipyridyl disulphide and oxidized glutathione as references.

As the mobile phase there was used 10% benzene-10% acetic acid-60% ethanol-20% water. Subsequent to chromatography, the thin layers were coloured with iodine and ninhydrin respectively.

TABLE 4

| Sample | Rf | Positive colour reaction with |
| --- | --- | --- |
| 2-thiopyridone | 0.79 | iodine |

TABLE 4-continued

| Sample | Rf | Positive colour reaction with |
| --- | --- | --- |
| 2-2-dipyridyl disulphide | 0.84 | iodine |
| oxidized glutathione | 0.11 | ninhydrin |
| 2-thiopyridyl glutathione | 0.43 | iodine, ninhydrin |

All samples each gave only one stain subsequent to development of the thin layer.

EXAMPLE 7

Conjugation of fragments of antibodies with β-galactosidase: The use of the conjugate in assaying IgE-titer in serum β-galactosidase from E. coli (Sigma 32.1.23 from Sigma Chemical Company, St. Louis, Mo., USA) was purified by covalent chromatography on a pyridyl disulphide-agarose gel (activated thiol Sepharose ® 4B from Pharmacia Fine Chemicals AB, Uppsala, Sweden) (Biochem. J. 133 (1973) 573–584). The enzyme was adsorbed on the gel at pH=8.0 and desorbed with 0.5M mercaptoethanol with 2 mM magnesium chloride, pH 8.0. Subsequent to desorption, the enzyme was salted-off on a column packed with dextran cross-linked with epichlorohydrin (Sephadex ® G-25M from Pharmacia Fine Chemicals AB, Uppsala, Sweden) in 0.2M sodium phosphate buffer, pH 8.0, with 2 mM magnesium chloride added. A solution containing 2.36 μM enzyme having a thiol-substitution degree of 24 equivalents thiol-groups/equivalent enzyme was obtained. 1.4 ml of the enzyme solution were mixed with thiopyridyl disulphide-containing fragments of rabbit-antihuman IgE-antibodies (c.f. Example 2), for conjugation through thiol-disulphide-exchange reaction (Biochem. J. 173 (1978) 723–737). After reacting for 96 hours at +4° C., the reaction mixture was chromatographed on a column packed with 109 ml of allyl dextran cross-linked with N,N'-methylene-bisacrylamide (Sephacryl ® S-300 from Pharmacia Fine Chemicals AB, Uppsala, Sweden) in 20 mM sodium phosphate buffer, pH 7.4, with 0.3M saline and 0.02% sodium azide added. A pool having an elution volume in the range of 39.4–55.2 ml with $A_{280}=0.038$ was collected. The pool was diluted 40 times in 20 mM sodium phosphate buffer, pH 7.4, with 0.3M saline, 0.1% human serum albumin (Sigma A 2386 from Sigma Chemical Company, St. Louis, Mo., USA), 0.1% Tween 20 and 0.02% sodium azide added. The diluted pool was then tested with components from a Phadezym ® IgE PRIST Test Kit (from Pharmacia Diagnostics AB, Uppsala, Sweden). The test was carried out in accordance with the instructions given for the IgE-test, although the β-galactosidase-anti-IgE-antibody conjugate included in the aforesaid test kit was replaced with the diluted pool. An EJ serum having 41430 u IgE/ml diluted in the same buffer as the above conjugate was used as standard. The Phadezym ® IgE PRIST Test was run as a reference.

Assaying of clinical serum samples having IgE-concentrations in the region of 0.5–80 kU/l gave a high correlation between the series. In the case of the pool, non-specific adsorption of enzyme activity on the cellulose matrix, included in the test as a carrier, was only half the adsorption obtained in the reference.

EXAMPLE 8

Splitting of disulphide in IgE with 5,5'-dithiobis-(2-nitrobenzoic acid) and 5-thio-2-nitrobenzoic acid A 76 mM solution (in 0.1M sodium phosphate, pH 8.1) of 5,5'-dithiobis-(2-nitrobenzoic acid) (DTNB) was made 14 mM with respect to dithiothreitol (DDT) to generate in situ a solution containing DTNB and 5-thio-2-nitrobenzoic acid (TNB). The reaction mixture was 28 mM with respect to TNB and 62 mM with respect to DTNB. A solution which was 0.65 mM with respect to TNB and 12 mM with respect to DTNB was prepared in the same manner. 0.2 ml of $1.75 \cdot 10^{-4}$M solutions of rabbit-IgG (from Miles Scandinavia Birkerod, Denmark) in 0.1M sodium phosphate buffer, pH 8.0, were then added to 0.8 ml portions of the reagent mixtures. Reaction mixtures were de-salted after different periods of time on columns packed with dextran cross-linked with epichlorohydrin (Sephadex ® G-25 Fine from Pharmacia Fine Chemicals AB, Uppsala, Sweden) in 0.1M sodium phosphate buffer, pH 8.0. The protein fractions were collected, whereafter the protein content of said fractions and the number of groups therein which could be split reductively to TNB were determined. The ratio between the determined concentrations is given as degree of substitution (number of equivalents of groups splittable to TNB per equivalent IgG).

TABLE 5

| Incubation time (mins) | Degree of substitution | |
| --- | --- | --- |
| | Reaction in 0.52 mM TNB and 9.6 mM DTNB | Reaction in 22 mM TNB and 50 mM DTNB |
| 45 | 0.57 | 3.6 |
| 85 | 0,77 | 4.1 |
| 120 | 1.08 | 4.4 |
| 180 | 1.34 | 4.7 |
| 375 | 1.79 | 5.3 |
| 19 × 60 | 2.32 | 6.0 |

EXAMPLE 9

Splitting of disulphides in IgG from sheep with 6,6'-dithionicotinic acid (C-PDS) and 6-thionicotinic acid (C-TP)

Dithiothreitol was added to 37 mM solutions of C-PDS (from EgaChemie, Steinheim, Federal Republic of Germany) in 0.1M sodium phosphate of differing pH-values according to Table 6 below, to a final concentration of 5 mM, to reduce a 5 mM fraction of the C-PDS-solution to 10 mM of the corresponding thion, C-TP. Dithiothreitol reduces disulphides in solution quantitatively to corresponding reduced forms (Biochem. 3. (1964) 480). 0.1 ml of $1.44 \times 10^{-4}$M solutions of sheep-IgG (from Miles Scandinavia, Birkerod, Denmark) in distilled water were added to 0.4 ml portions of these reagent solutions. The solutions were incubated for 18 hrs at 23° C., whereafter they were de-salted on columns packed with dextran cross-linked with epichlorohydrin (Sephadex ® G-25 Fine from Pharmacia Fine Chemicals AB, Uppsala, Sweden) in 0.1M sodium phosphate buffer, pH 8.1, the protein fractions being collected. The protein content of the fractions and the amount of groups therein capable of being split reductively to C-TP were then determined spectrophotometrically, and the values of the degrees of substitution subsequently calculated. The following molar extinction coefficients were used:

$E_{342} = 9400$ for C-TP
$E_{280} = 221\,000$ for IgG
$E_{280} = 6000$ was added to $E_{280}$ for IgG for each equivalent C-TP introduced.

TABLE 6

| Incubation-pH | Degree of substitution (equivalents of groups splittable to O-TP/IgG equivalent |
|---|---|
| 6.9 | 1.15 |
| 7.6 | 2.56 |
| 7.9 | 2.90 |
| 8.5 | 3.46 |
| 9.0 | 3.82 |
| 9.8 | 4.12 |

We claim:

1. A method for splitting at least one disulphide bond —S—S—, where each of the sulphur atoms is directly bound covalently to its respective aliphatic carbon atom in an organic substance which contains at least one such disulphide bond, in which each bond —S—S— which is split is converted substantially to two reactive groups of the formulae —S—S—$R_1$ and $R_2$—S—S—, where $R_1$ and $R_2$ are equal or different and each is an organic residue, characterized by splitting said at least one bond by reacting said organic substance with a mixture of a compound $R_3$—S—S—$R_4$ and a compound capable of existing in the tautomeric forms $R_5$—S—H and $HR_5'$=S or corresponding resonance-stabilized anion form, in which compounds the residues $R_3$, $R_4$ and $R_5$
   (i) are organic residues of which all are different, two are equal or all are equal, and
   (ii) are defined in
      (a) that each of the aforesaid sulphur atoms in the compounds $R_3$—S—S—$R_4$ and $R_5$—S—H is bound to a carbon atom in an aromatic ring and
      (b) that under splitting conditions a compound $R_3$—S—H or $R_4$—S—H released by the reaction of the compound $R_3$—S—S—$R_4$ and the compound $R_5$—S—H exist substantially in their tautomeric forms $HR_3'$=S, $HR_4'$=S and $HR_5'$=S respectively, or corresponding resonance-stabilized anion forms, and that $R_1$ and $R_2$ each constitute a residue belonging to the group consisting of $R_3$, $R_4$ and $R_5$.

2. A method according to claim 1, characterized in that the organic substance is a polypeptide.

3. A method according to claim 2, characterized in that the polypeptide is an immunoglobulin or a fragment thereof.

4. A method according to claim 3, characterized in that the immunoglobulin is an antibody or an antibody-active fragment thereof.

5. A method according to claim 1, characterized in that $R_1 = R_2 = R_3 = R_4 = R_5$.

* * * * *